United States Patent [19]

Willmund et al.

[11] 4,270,987
[45] Jun. 2, 1981

[54] ACID GALVANIC NICKEL BATHS CONTAINING N-(2,3-DIHYDROXYPROPYL)-PYRIDINIUM SULFATES

[75] Inventors: Wolf-Dieter Willmund, Düsseldorf; Heinz Wagner, Hilden, both of Fed. Rep. of Germany

[73] Assignee: Henkel Kommanditgesellschaft auf Aktien, Düsseldorf-Holth ausen, Fed. Rep. of Germany

[21] Appl. No.: 125,246

[22] Filed: Feb. 27, 1980

Related U.S. Application Data

[62] Division of Ser. No. 66,568, Aug. 15, 1979, abandoned.

[30] Foreign Application Priority Data

Aug. 21, 1978 [DE] Fed. Rep. of Germany ....... 2836581

[51] Int. Cl.³ .............................................. C25D 3/18
[52] U.S. Cl. ...................................... 204/49; 546/339
[58] Field of Search ................ 204/49, 112; 106/1.27; 546/339

[56] References Cited

U.S. PATENT DOCUMENTS 2,647,866  8/1953  Brown ...................................... 204/49
3,314,868  4/1967  Willmund et al. ...................... 204/49

*Primary Examiner*—G. L. Kaplan
*Attorney, Agent, or Firm*—Hammond & Littell, Weissenberger & Muserlian

[57] ABSTRACT

This invention is directed to N-(2,3-dihydroxypropyl)-pyridinium sulfates of the formula

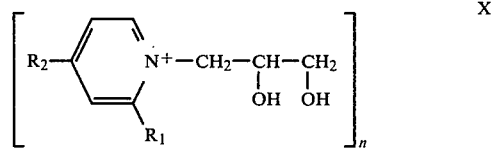

wherein $R_1$ and $R_2$, which may be the same or different, are a hydrogen atom or a methyl radical; X is the acid radical $SO_4^=$ or $HSO_4^-$; and n is 1 or 2. This invention is also directed to the preparation of these compounds and their use in acid galvanic nickel baths.

5 Claims, No Drawings

ACID GALVANIC NICKEL BATHS CONTAINING N-(2,3-DIHYDROXYPROPYL)-PYRIDINIUM SULFATES

This is a division of Ser. No. 066,568 filed Aug. 15, 1979 and now abandoned.

FIELD OF THE INVENTION

A subject of this application is N-(2,3-dihydroxypropyl)-pyridinium sulfates. Also subjects of this application are the method of preparing the compounds and their use in an acid galvanic nickel bath.

BACKGROUND OF THE INVENTION

It is known to use quaternary ammonium salts derived from heterocyclic nitrogen-containing compounds such as pyridine, quinoline, isoquinoline, or quinaldine, as galvanic additives in acid nickel baths. The nickel coats produced by use of these additives are frequently brittle or show mat zones in their low current density regions, and thus do not meet the demands made on them.

Furthermore, it is known to use reaction products of heterocyclic nitrogen-containing compounds of the aromatic type with sultones as leveling agents in galvanic nickel baths. These products represent, on the basis of their chemical constitution, inner salts of aminoalkane sulfonic acids, so-called sulfobetaines. The leveling effect of these products is quite satisfactory; however, they are subject to decomposition under certain circumstances, which may impair the leveling effect.

The problem has therefore been to find products which likewise yield satisfactory leveling effects without being relatively susceptible to decomposition in the acid galvanic nickel bath. Applicants have surprisingly developed pyridinium sulfate compounds that function as suitable leveling agents in acid galvanic nickel baths and have satisfactory decomposition properties. In addition, the pyridinium sulfate compounds developed have the advantage of simple preparation that does not require propane sultone.

OBJECTS OF THE INVENTION

It is an object of this invention to provide novel pyridinium sulfate compounds.

It is also an object of this invention to provide a method of preparing the novel pyridinium compounds.

It is further an object of this invention to provide pyridinium sulfate compounds useful in acid galvanic nickel baths.

These and other objects of the invention will become more apparent in the discussion below.

DETAILED DESCRIPTION OF THE INVENTION

The subjects of the invention are N-(2,3-dihydroxypropyl)-pyridinium sulfates, their preparation, and their use as leveling agents in acid galvanic nickel baths. The N-(2,3-dihydroxypropyl)-pyridinium sulfates have the formula

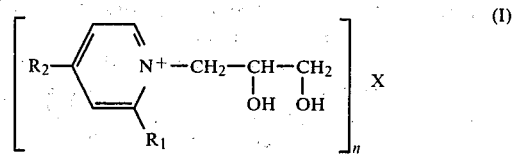

wherein $R_1$ and $R_2$, which may be the same or different, are a hydrogen atom or a methyl radical; X is the acid radical $SO_4^=$ or $HSO_4^-$; and n is 1 or 2.

The neutral sulfates of Formula I are obtained by converting a pyridine compound of the formula

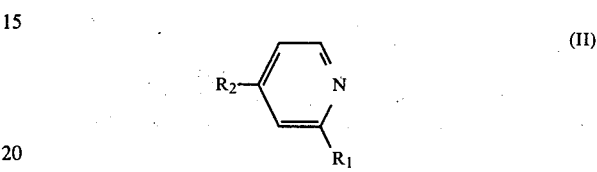

wherein $R_1$ and $R_2$ are as described above, to the sulfate with sulfuric acid and then reacting the sulfate with glycidol. The acid sulfates can be obtained by quaternizing a pyridine compound of Formula II, i.e., pyridine or a substituted pyridine compound, with glycerin chlorohydrin to obtain a quaternary ammonium salt mixing the quaternary ammonium salt with sulfuric acid, and removing the released hydrochloric acid.

The baths obtained with the products of the invention can be subjected to extremely high bath loads without decomposition products being formed. In addition, the baths produced with the products of the invention are characterized by excellent leveling depth dispersion.

Of particular importance among the N-(2,3-dihydroxypropyl)-pyridinium sulfates, both in terms of availability and effectiveness, are N-(2,3-dihydroxypropyl)-pyridinium sulfates, especially the acid sulfate.

The concentrations in which the new compounds according to the invention are used are from about 0.05 to 3 g per liter, preferably from about 0.1 to 0.5 g per liter, of bath liquor. The applicable current densities range from about 0.1 to 9 $A/dm^2$ with an operating temperature of about 50° to 60° C.

In addition to the leveling agents according to the invention, conventional basic lustering agents, such as benzene-m-disulfonic acid, diaryl disulfimides, sulfonamides, saccharin, and the like, can be added to the acid galvanic nickel baths.

EXAMPLES

The preparation of useful compounds according to the invention is described in the following examples:

EXAMPLE 1

Preparation of bis-N-(2,3-dihydroxypropyl)-pyridinium sulfate

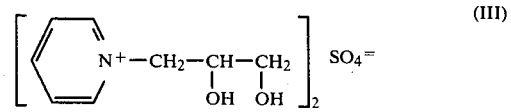

Seventy-nine grams of pyridine (1 mol) were charged and mixed under cooling at about 20° C. with a mixture of 49 g of conc. sulfuric acid and 130 g of water (0.5 mol). After the mixture was heated to 40° C., 74 g of glycidol (1 mol) were added slowly in drops over a period of 45 minutes. The temperature rose to 50° C. Then, the reaction mixture was stirred for five hours at 70° C. and subsequently concentrated under vacuum. An amount of 180 g of a thickly liquid, slightly yellowish-green reaction product was obtained. The product had the following refractive index: $n_D^{20} = 1.5140$.

For use in galvanic nickel baths, a 20% aqueous solution of the reaction product was prepared.

The reaction product can also be worked up from the reaction mixture by treatment with steam. After steam is blown into the reaction mixture, the amount of active substance, i.e., reaction product, is determined in an aliquot portion. Then the solution contents are adjusted to 20% by weight solid substance by the addition of water.

In analogy to the above-described procedure, α-picoline was used as a starting material to prepare bis-N-(2,3-dihydroxypropyl)-α-picolinium sulfate, which has the formula

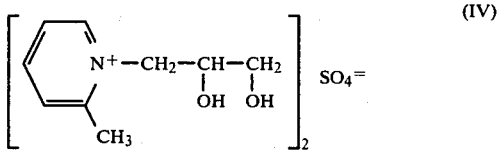

This compound was found to have a refractive index of $n_D^{20} = 1.5268$. Similarly, γ-picoline was used as a starting material to prepare bis-N-(2,3-dihydroxypropyl)-γ-picolinium sulfate, which has the formula

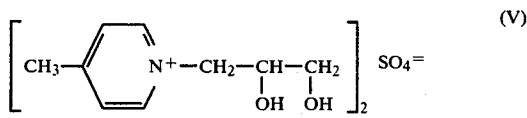

and which had a refractive index of $n_D^{20} = 1.5272$.

The use of α,γ-lutidine as a starting material resulted in the preparation of the compound bis-N-(2,3-dihydroxypropyl)-α,γ-lutidinium sulfate, which has the formula

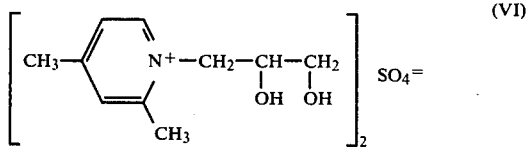

EXAMPLE 2

N-(2,3-dihydroxypropyl)-pyridinium hydrogensulfate

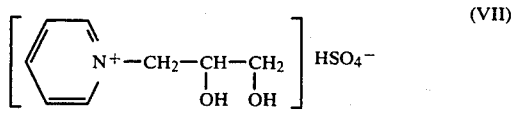

Seventy-nine grams (1 mol) of pyridine were charged and mixed at 100° C. under stirring with 110.5 g (1 mol) of α-glycerin chlorohydrin. The stirring was continued for five hours at 100° to 110° C. After the reaction mixture was cooled, the product was taken up in water, and steam was blown through to remove any unreacted pyridine residue. Then, a molar amount of conc. sulfuric acid was added. On concentration in vacuum, the hydrochloric acid released was removed. For use in galvanic baths, a 20% solution was prepared.

The pure substance was obtained in crystalline form after the concentrated crude product was dissolved in hot ethanol and some water and the solution cooled overnight. The product represented a practically white finely crystalline loose powder which melted at 184° to 186° C.

In a similar manner, N-(2,3-dihydroxypropyl)-α-picolinium hydrogensulfate, N-(2,3-dihydroxypropyl)-γ-picolinium hydrogensulfate, and N-(2,3-dihydroxypropyl)-α,γ-lutidinium hydrogensulfate can be obtained.

The following Examples set forth nickel baths using the compounds according to the invention.

EXAMPLE 3

An amount of 2 g/l o-toluene disulfonimide as a basic lustering agent, 0.5 g/l of sodium dodecyl sulfate as a wetting agent, and 0.25 g/l of bis-N-(2,3-dihydroxypropyl)pyridinium sulfate as a leveling agent was added to a Watts-type nickel bath. At a bath temperature of 50° to 60° C. in the current density range of 0.5 to 9 A/dm², high-luster, greatly leveled nickel deposits of good ductility were obtained. After bath loads of 1000 Ah/l, decomposition products could not be detected in the baths.

Instead of bis-N-(2,3-dihydroxypropyl)-pyridinium sulfate, the following products can be used with equally good results in the same concentration:

bis-N-(2,3-dihydroxypropyl)-α-picolinium sulfate,
bis-N-(2,3-dihydroxypropyl)-γ-picolinium sulfate, and
bis-N-(2,3-dihydroxypropyl)-α,γ-lutidinium sulfate, and with particular advantage,
bis-N-(2,3-dihydroxypropyl)-pyridinium hydrogen sulfate.

EXAMPLE 4

An amount of 1.5 g/l of N-(benzene sulfonyl)acetamide as a basic lustering agent, 0.5 g/l of sodium dodecyl sulfate as a wetting agent, and 0.3 g/l bis-N-(2,3-dihydroxypropyl)-pyridinium sulfate as a leveling agent was added to a Watts-type nickel bath. At bath temperature of 50° to 60° C. in the current density range of from 0.1 to 9 A/dm², high-luster, well-leveled nickel deposits of good ductility were obtained. A similar bath having the corresponding acid sulfate likewise yielded high-quality nickel deposits.

The following nickel baths lead to equally good results:

EXAMPLE 5

| Component | Concentration (g/l) |
|---|---|
| Nickel sulfate (NiSO₄ . 7 H₂O) | 270 |
| Nickel chloride (NiCl₂ . 6 H₂O) | 65 |
| Boric acid | 35 |
| Sodium dodecyl sulfate | 0.5 |
| Saccharin | 4.0 |
| Bis-N-(2,3-dihydroxypropyl)-pyridinium sulfate | 0.5 |

EXAMPLE 6

| Component | Concentration (g/l) |
| --- | --- |
| Nickel sulfate (NiSO$_4$ . 7 H$_2$O) | 140 |
| Nickel chloride (NiCl$_2$ . 6 H$_2$O) | 110 |
| Boric acid | 40 |
| Saccharin | 6 |
| Isononyl sulfate, Na-salt | 0.3 |
| Bis-N-(2,3-dihydroxypropyl)-α-picolinium sulfate | 0.2 |

EXAMPLE 7

| Component | Concentration g/l |
| --- | --- |
| Nickel sulfate (NiSO$_4$ . 6 H$_2$O) | 280 |
| Nickel chloride (NiCl$_2$ . 6 H$_2$O) | 65 |
| Boric acid | 35 |
| Sodium dodecyl sulfate | 0.3 |
| Saccharin | 6 |
| Propargyl alcohol | 0.013 |
| Allyl sulfonate | 1.0 |
| Bis-N-(2,3-dihydroxypropyl)-γ-picolinium sulfate | 0.3 |

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

We claim:

1. An aqueous acid galvanic nickel bath composition having lustering and wetting agents, characterized in that the bath contains as a leveling agent an N-(2,3-dihydroxypropyl)-pyridinium sulfate of the formula

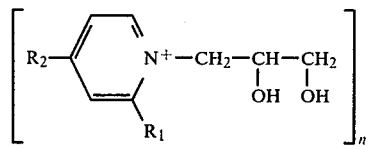

wherein R$_1$ and R$_2$, which may be the same or different, are a hydrogen atom or a methyl radical; X is the acid radical SO$_4$= or HSO$_4$−; and n is a digit sufficient to satisy the valence of X.

2. The acid galvanic nickel bath of claim 1 wherein the sulfate is present in an amount of from about 0.05 to 3 g/l of bath liquor.

3. The acid galvanic nickel bath of claim 2 wherein the sulfate is present in an amount of from about 0.1 to 0.5 g/l of bath liquor.

4. The acid galvanic nickel bath of claim 2 wherein the sulfate is bis-N-(2,3-dihydroxypropyl)-pyridinium sulfate.

5. The acid galvanic nickel bath of claim 2 wherein the sulfate is N-(2,3-dihydroxypropyl)-pyridinium hydrogen sulfate.

* * * * *